United States Patent [19]

VandenBerg

[11] Patent Number: Plant 6,882

[45] Date of Patent: Jun. 27, 1989

[54] CHRYSANTHEMUM PLANT NAMED OREO

[75] Inventor: Cornelis P. VandenBerg, Salinas, Calif.

[73] Assignee: Yoder Brothers, Inc., Barberton, Ohio

[21] Appl. No.: 173,083

[22] Filed: Mar. 25, 1988

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Oreo particularly characterized by its flat capitulum form; daisy capitulum type; purple ray floret color; diameter across face of capitulum of up to 7 cm at maturity; uniform eight week photoperiodic flowering response to short days; peduncle length ranging from 10 to 15 cm on open, terminal sprays; short plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora,* and referred to by the cultivar name Oreo.

Oreo, identified as 83486003, was originated from a cross made by Cornelis P. VandenBerg in a controlled breeding program in Salinas, Calif. in 1982.

The female parent and the male parent of Oreo were both unnamed seedlings, identified respectively as 78*95004 and 79T38005.

Oreo was discovered and selected as one flowering plant within the progeny of the stated cross by Cornelis P. VandenBerg in July 1983 in a controlled environment in Salinas, Calif.

The first act of asexual reproduction of Oreo was accomplished when vegetative cuttings were taken from the initial selection in September 1983 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Oreo are firmly fixed and are retained through successive generations of asexual reproduction.

Oreo has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Oreo, which, in combination, distinguish this Chrysanthemum as a new and distinct cultivar:

1. Flat capitulum form.
2. Daisy capitulum type.
3. Purple ray floret color.
4. Diameter across face of capitulum up to 7 cm at maturity.

5. Uniform eight week photoperiodic flowering response to short days.
6. Peduncle length ranging from 10 to 15 cm on open terminal sprays.
7. Short plant height, requiring two to three long day weeks prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Oreo, with the colors being as nearly true as possible with illustrations of this type.

Sheet 1 is a color photograph of Oreo grown as a single stem cut spray mum.

Sheet 2 is a black and white photograph of three views of the inflorescence of Oreo.

Sheet 3 is a black and white photograph showing the upper and under sides of the leaves of Oreo at three stages of development (mature, intermediate and immature).

Of the commercial cultivars known to the inventor, the most similar in comparison to Oreo is Pink Marble. Reference is made to Chart A, which compares certain characteristics of Oreo to the sme characteristics of Pink Marble.

Similar traits are ray floret color and capitulum form and type. The peduncle length of Oreo is shorter, the diameter of capitulum is smaller, plant height is less and the flowering response period is shorter than Pink Marble. Under adverse conditions Pink Marble exhibits compounding of the spray formation and develops bract tissue in the disc. The spray formation of Oreo is always terminal, with no development of bracts.

In the following description, color references are made to The Royal Horticultural Society Colour Chart. The color values were determined on plant material grown in Salinas, Calif. on Oct. 20, 1987.

Classification:

*Botanical.*—*Dendranthema grandiflora,* cv Oreo.

*Commercial.*—Daisy cut spray mum.

INFLORESCENCE

A. Capitulum:

*Form.*—Flat.
*Type.*—Daisy.
*Diameter across face.*—Up to 7 cm at maturity.

B. Corolla of ray florets:
*Color (general tonality from a distance of three meters).*—Purple.
*Color (upper surface).*—75B to 75C.
*Color (under surface).*—75D.
*Shape.*—Flat; oblong.

C. Corolla of disc florets:
*Color (mature).*—Closest to 14A.
*Color (immature).*—Closest to 144B.

D. Reproductive organs:
*Androecium.*—Present on disc florets only; moderate pollen.
*Gynoecium.*—Present on both ray and disc florets.

PLANT

A. General appearance:
*Height.*—Short; 90 to 100 cm as a single stem cut mum with 2 to 3 long day weeks prior to short days.

B. Foliage:
*Color (upper surface).*—147A.

*Color (under surface).*—147B.
*Shape.*—Deeply lobed and serrated.

CHART A

COMPARISON OF OREO AND PINK MARBLE

| | Oreo | Pink Marble |
|---|---|---|
| Ray floret color | Purple | Purple |
| Capitulum form and type | Flat<br>Daisy | Flat<br>Daisy |
| Spray formation | Terminal<br>10 to 15 cm peduncles | Terminal to Compound<br>20 to 25 cm peduncles |
| Diameter across face of capitulum | Up to 7 cm | Up to 83 mm |
| Plant height | Short | Medium |
| Flowering response period | 8 weeks | 9 weeks |
| Low temperature tolerance | Excellent | Good |

COMPARISONS MADE OF PLANTS GROWN AS SINGLE STEM SPRAY CUT MUMS IN SALINAS, CALIFORNIA

I claim:

1. A new and distinct Chrysanthemum plant named Oreo, as described and illustrated, and parts thereof.

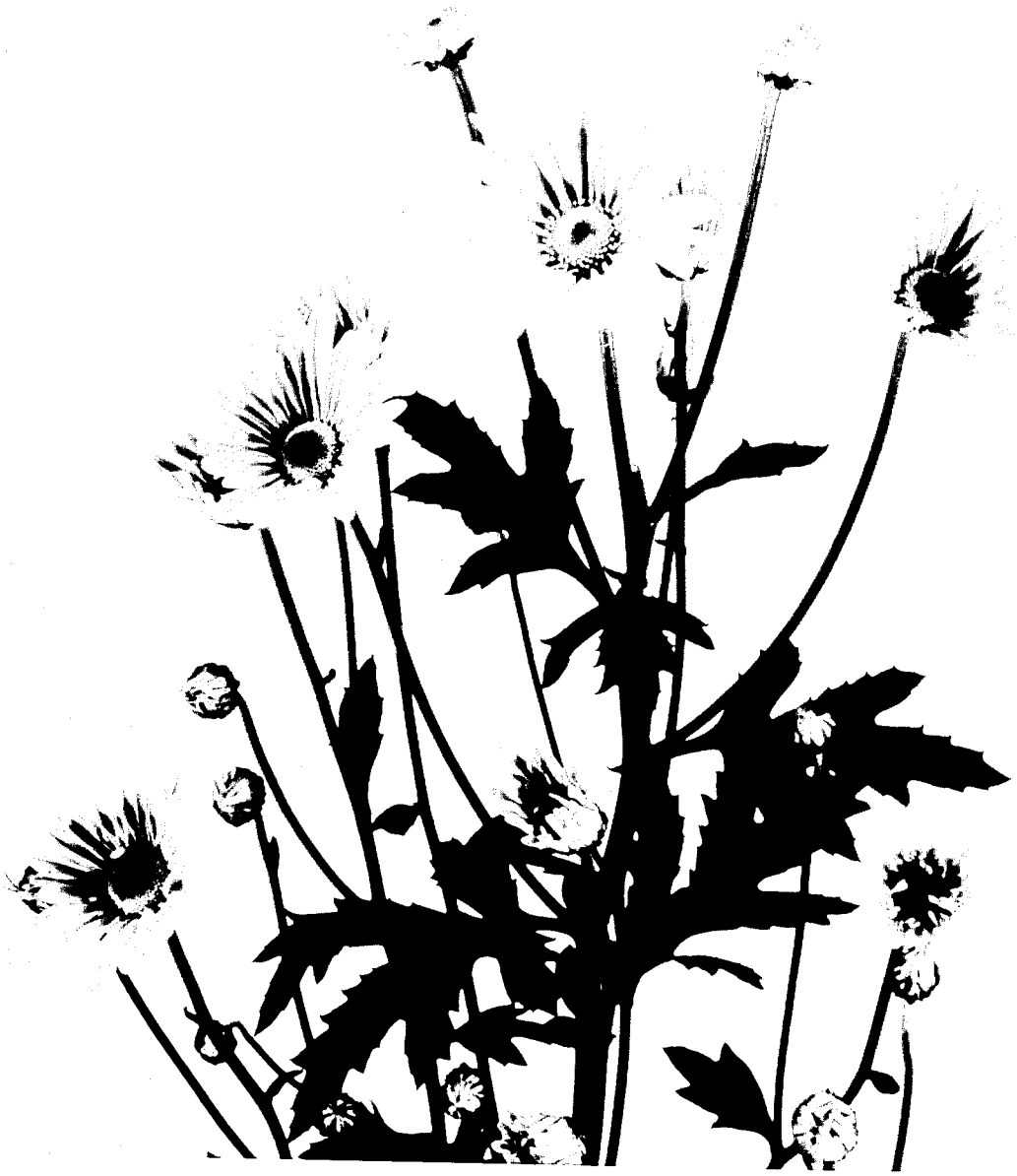

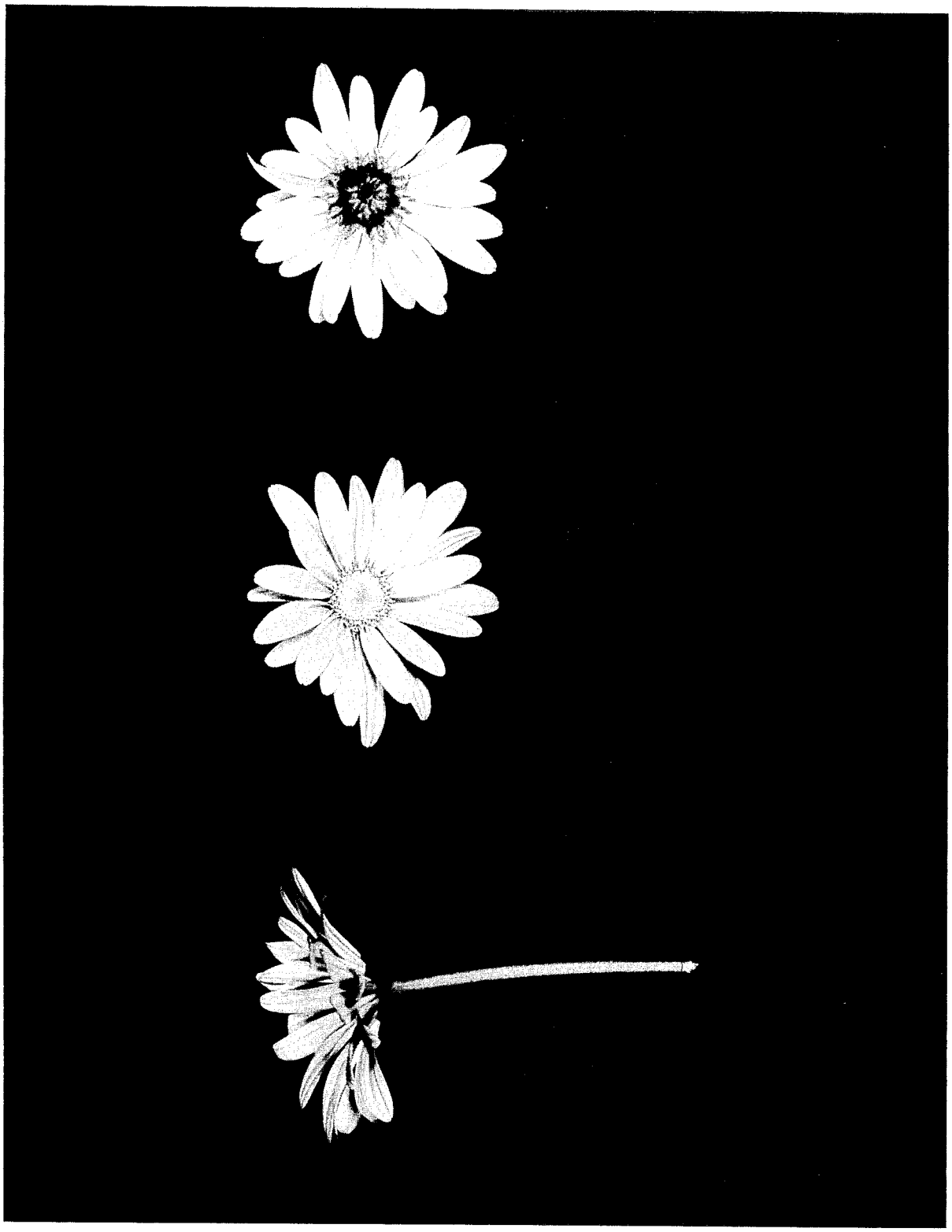

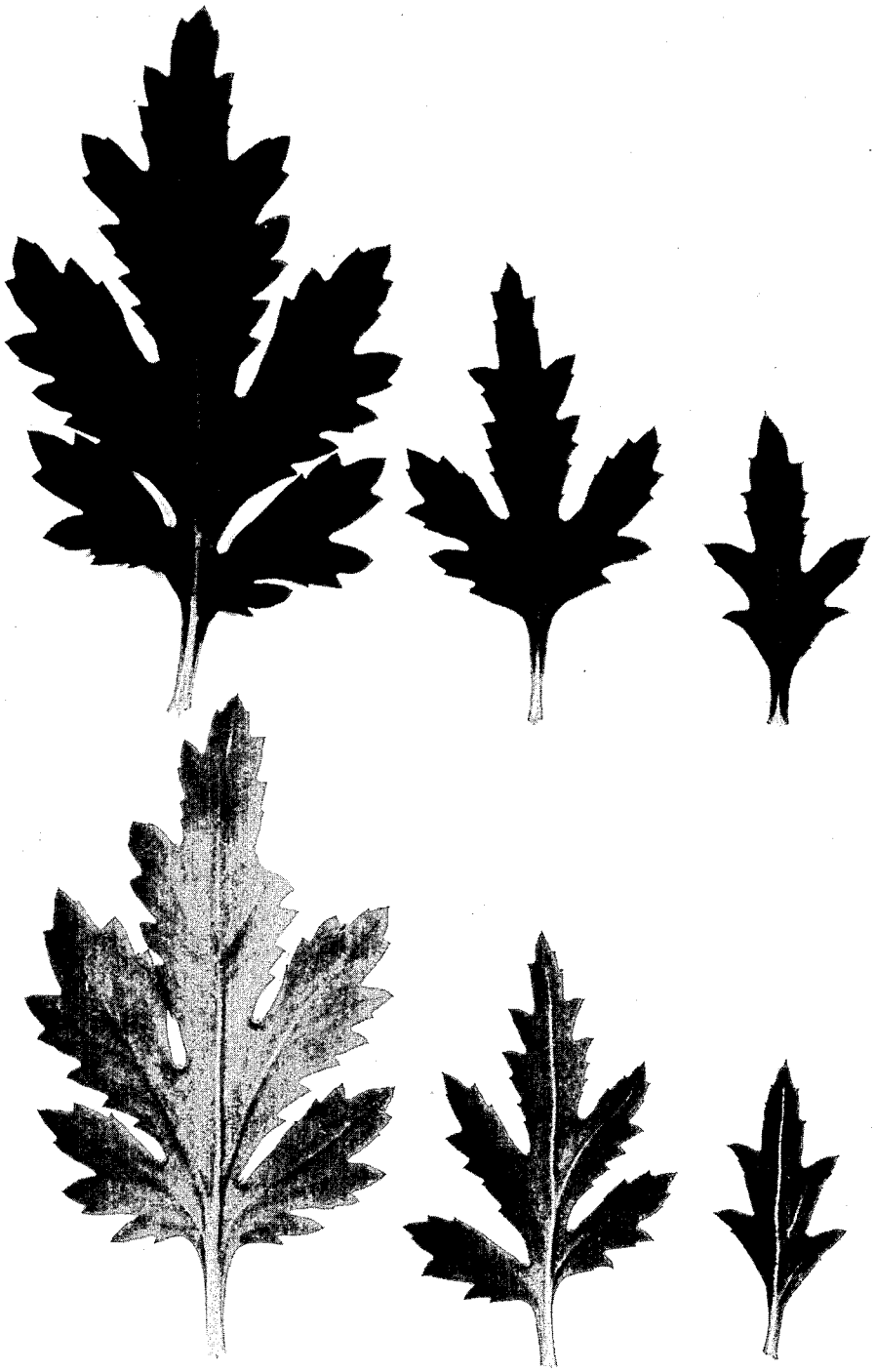

* * * * *